(12) United States Patent
Chien et al.

(10) Patent No.: US 9,901,697 B2
(45) Date of Patent: Feb. 27, 2018

(54) RESPIRATORY MASK

(71) Applicant: APEX MEDICAL CORP., New Taipei (TW)

(72) Inventors: Chih-Tsan Chien, New Taipei (TW); Ying-Chieh Hsu, New Taipei (TW)

(73) Assignee: APEX MEDICAL CORP., New Taipei (TW)

(*) Notice: Subject to any disclaimer, the term of this patent is extended or adjusted under 35 U.S.C. 154(b) by 481 days.

(21) Appl. No.: 14/459,518

(22) Filed: Aug. 14, 2014

(65) Prior Publication Data

US 2015/0059763 A1 Mar. 5, 2015

Related U.S. Application Data

(60) Provisional application No. 61/873,776, filed on Sep. 4, 2013.

(51) Int. Cl.
*A61M 16/06* (2006.01)
*A61M 16/20* (2006.01)
*A61M 16/08* (2006.01)

(52) U.S. Cl.
CPC .... *A61M 16/0633* (2014.02); *A61M 16/0683* (2013.01); *A61M 16/0816* (2013.01);
(Continued)

(58) Field of Classification Search
CPC .......... A61M 16/0003; A61M 16/0051; A61M 16/0057; A61M 16/0066; A61M 16/0069; A61M 16/0078; A61M 16/0084; A61M 16/0415; A61M 16/0463; A61M 16/0488; A61M 16/0493; A61M 16/06; A61M 16/0605; A61M 16/0611; A61M 16/0616; A61M 16/0622; A61M 16/0633; A61M 16/0638; A61M 16/0644; A61M 16/065; A61M 16/0666; A61M 16/0683; A61M 16/0694; A61M 16/08; A61M 16/0816; A61M 16/0825; A61M 16/0833; A61M 16/0841; A61M 16/085; A61M 16/0858;
(Continued)

(56) References Cited

U.S. PATENT DOCUMENTS

| 5,921,239 A * | 7/1999 | McCall | A61M 16/06 128/205.25 |
| 7,934,501 B2 * | 5/2011 | Fu | A61M 16/08 128/205.25 |

(Continued)

FOREIGN PATENT DOCUMENTS

WO  WO 2013006899 A1 * 1/2013 ............ A61M 16/06

*Primary Examiner* — Annette Dixon
(74) *Attorney, Agent, or Firm* — Muncy, Geissler, Olds & Lowe, P.C.

(57) ABSTRACT

A respiratory mask includes a frame and an elbow engaged with the frame. The frame has a front surface and a rear surface. The front surface defines a connecting hole. The rear surface defines a receiving chamber. The connecting hole is in communication with the receiving chamber. The connecting hole is in communication with the receiving chamber at the rear surface. The elbow has a first end portion. The first end portion is connected with the connecting hole. The first end portion and the frame cooperatively define at least one air flow path communication air in the receiving chamber with external air.

21 Claims, 14 Drawing Sheets

(52) U.S. Cl.
CPC ....... *A61M 16/208* (2013.01); *A61M 16/0616* (2014.02); *A61M 16/0841* (2014.02); *A61M 16/0875* (2013.01); *A61M 2205/42* (2013.01)

(58) Field of Classification Search
CPC .......... A61M 16/0866; A61M 16/0875; A61M 16/0883; A61M 16/1045; A61M 16/1065; A61M 16/109; A61M 16/1095; A61M 16/16; A61M 16/20; A61M 16/208; A61M 2016/0027; A61M 2016/003; A61M 2016/0039; A61M 2016/0042; A61M 2016/0661; A61M 2202/0085; A61M 2202/0208; A61M 2202/0225; A61M 2205/332; A61M 2205/3331; A61M 2205/3334; A61M 2205/3375; A61M 2205/42; A61M 2205/52; A61M 2205/581; A61M 2205/583; A61M 2205/7527; A61M 2205/7536; A61M 2206/14; A61M 2206/20; A61M 2207/00; A61M 2207/10; A61M 2210/0618; A61M 2210/0625; A61M 25/10; A61M 35/00; A61M 39/10; A61M 39/1055

USPC ............ 128/201.22, 202.27, 202.28, 203.11, 128/203.12, 203.29, 204.18, 205.11, 128/205.12, 205.13, 205.14, 205.19, 128/205.25, 206.15, 206.21, 206.24, 128/206.26, 206.27, 206.28, 207.11, 128/207.12, 207.13, 207.14, 912

See application file for complete search history.

(56) References Cited

U.S. PATENT DOCUMENTS

| | | | |
|---|---|---|---|
| 2003/0094177 A1* | 5/2003 | Smith | A61M 16/06 128/204.18 |
| 2004/0025881 A1* | 2/2004 | Gunaratnam | A61M 16/06 128/206.15 |
| 2010/0258133 A1 | 10/2010 | Todd et al. | |
| 2011/0056495 A1* | 3/2011 | Ho | A61M 16/0816 128/204.18 |
| 2012/0138061 A1* | 6/2012 | Dravitzki | A61M 16/06 128/205.25 |
| 2013/0213401 A1* | 8/2013 | Haibach | A61M 16/06 128/205.25 |
| 2015/0151071 A1* | 6/2015 | Von Moger | A61M 39/1055 128/202.27 |

* cited by examiner

RESPIRATORY MASK

CROSS-REFERENCE TO RELATED APPLICATION

This application claims the benefit under 35 U.S.C. § 119(c) of U.S. Provisional Application No. 61/873,776, filed on Sep. 4, 2013, entitled "HUMIDIFIER for Respiratory Apparatus", the disclosure of which is incorporated by reference herein.

FIELD

The disclosure generally relates to a breathing apparatus, and particularly relates to a respiratory mask.

BACKGROUND

A respiratory mask is an apparatus providing breathable air for a user. The respiratory mask is connected with an air delivery conduit, and the air delivery conduit is connected with a blower. The blower provides pressurized air or other breathable air to the respiratory mask through the air delivery conduit. However, when the breathable air enters the respiratory mask, the breathable air directly rushes to a user's nose, in particular the nostrils, causing user discomfort. Generally, the whole apparatus needs air washout portions to allow exhaled air from user to exit the space defined by the mask frame. Said air washout portions are either on the mask or the elbow which connects with the mask and the air delivery conduit. The air washout portions are usually in the form of through holes or venting membranes. The through holes described here must allow air to vent out and at the same time keep the air pressurized, which lead to short-diameter and small sizes of the through holes. The tiny holes therefore constitute a portion that is hard to clean and may lead to accumulation of unwanted dirt or living organisms.

What is needed, therefore, is a respiratory mask to overcome the above described disadvantages.

BRIEF DESCRIPTION OF THE DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, like reference numerals designate corresponding parts throughout the several views.

DETAILED DESCRIPTION

Embodiments of a respiratory mask will now be described in detail below and with reference to the drawings.

Figure 1:
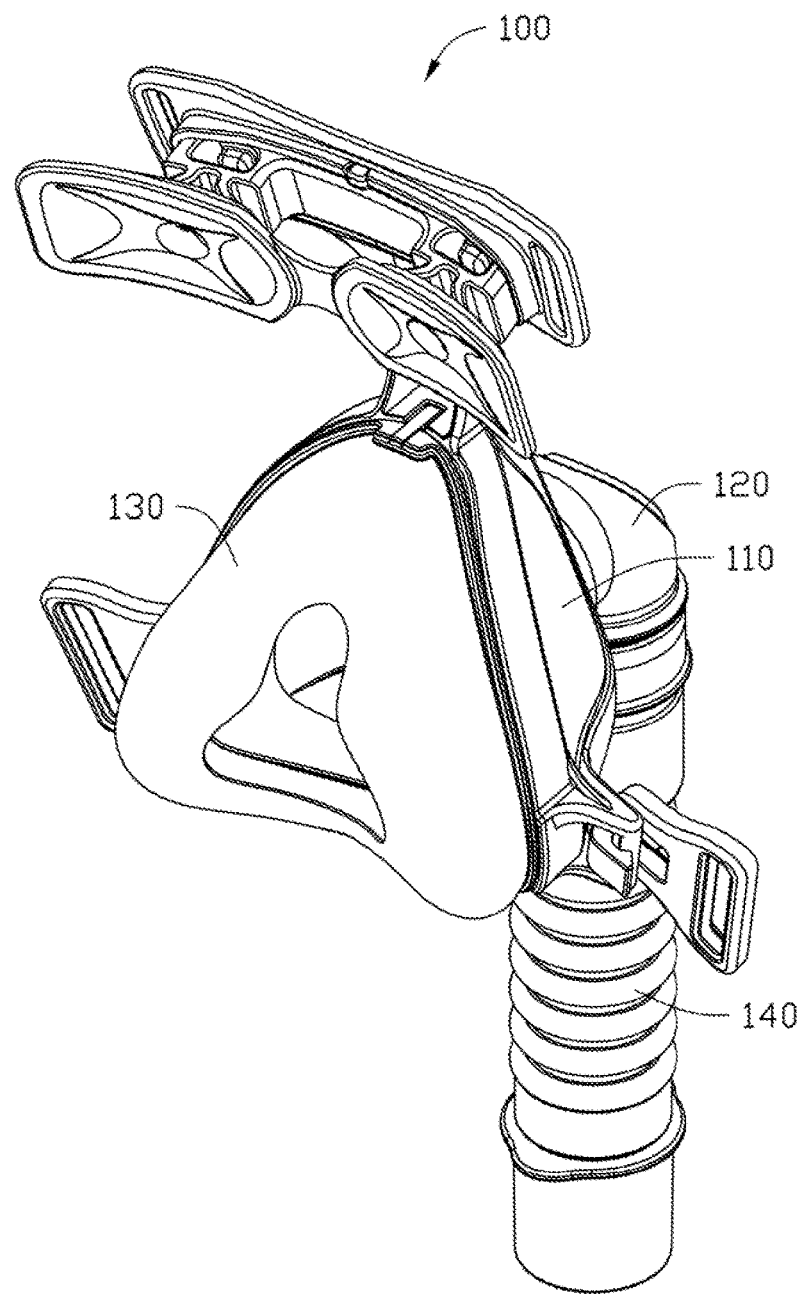
FIG. 1 is an isometric view of a respiratory mask in accordance with a first embodiment of the present disclosure.

Referring to FIG. 1, a respiratory mask 100 in accordance with a first embodiment is provided. The respiratory mask 100 includes a frame 110, an elbow 120, and a cushion 130, and an air delivery conduit 140.

Figure 2:
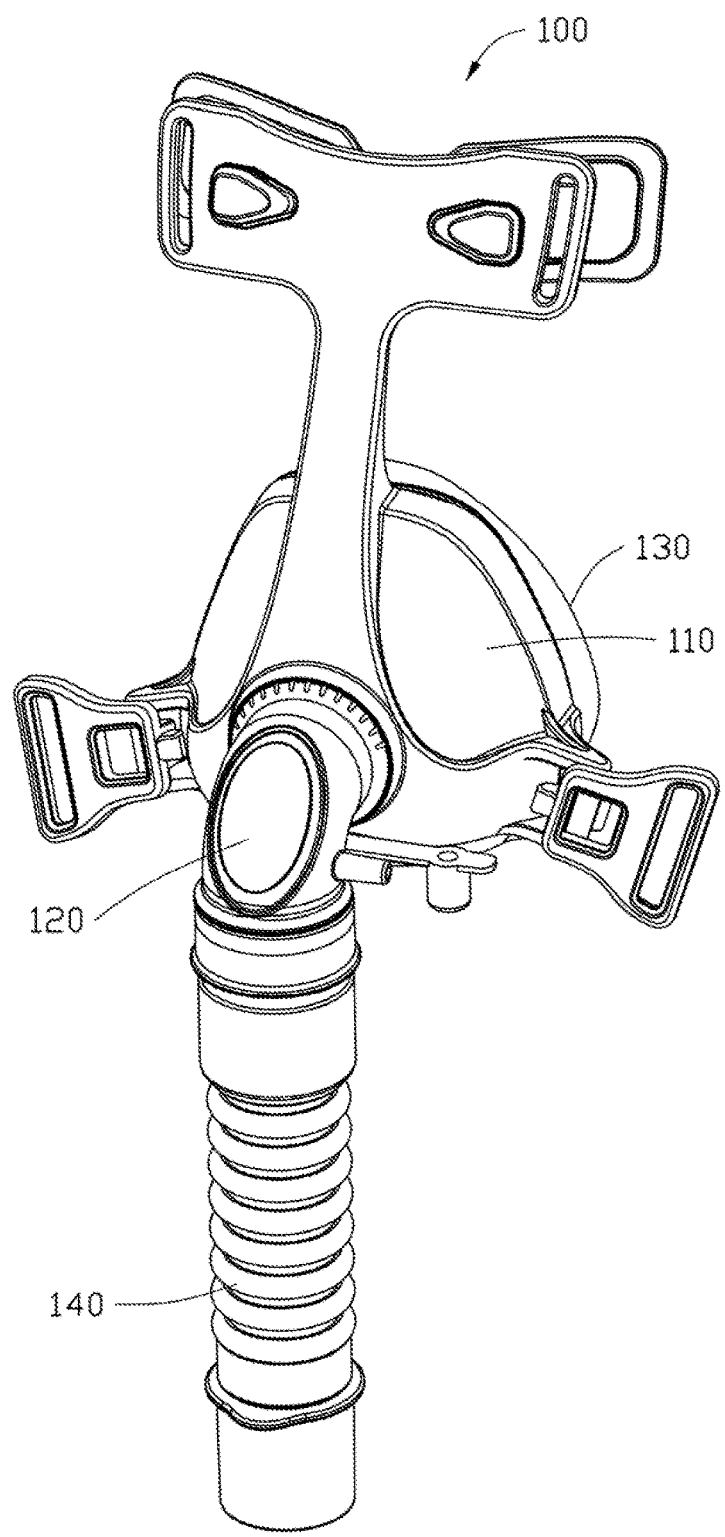
FIG. 2 is another assembled view of the respiratory mask in FIG. 1.
Figure 3:
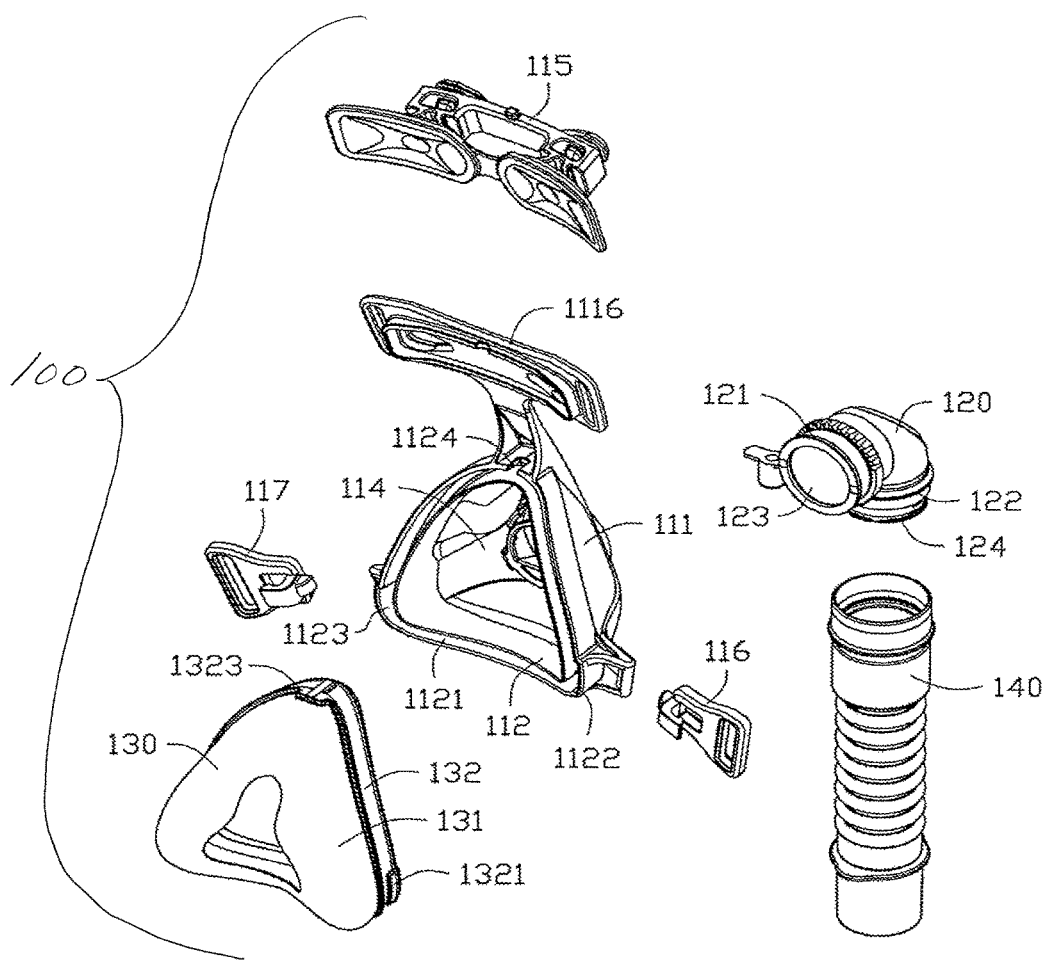
FIG. 3 is an exploded perspective view of the respiratory mask in FIG. 1.
Figure 4:
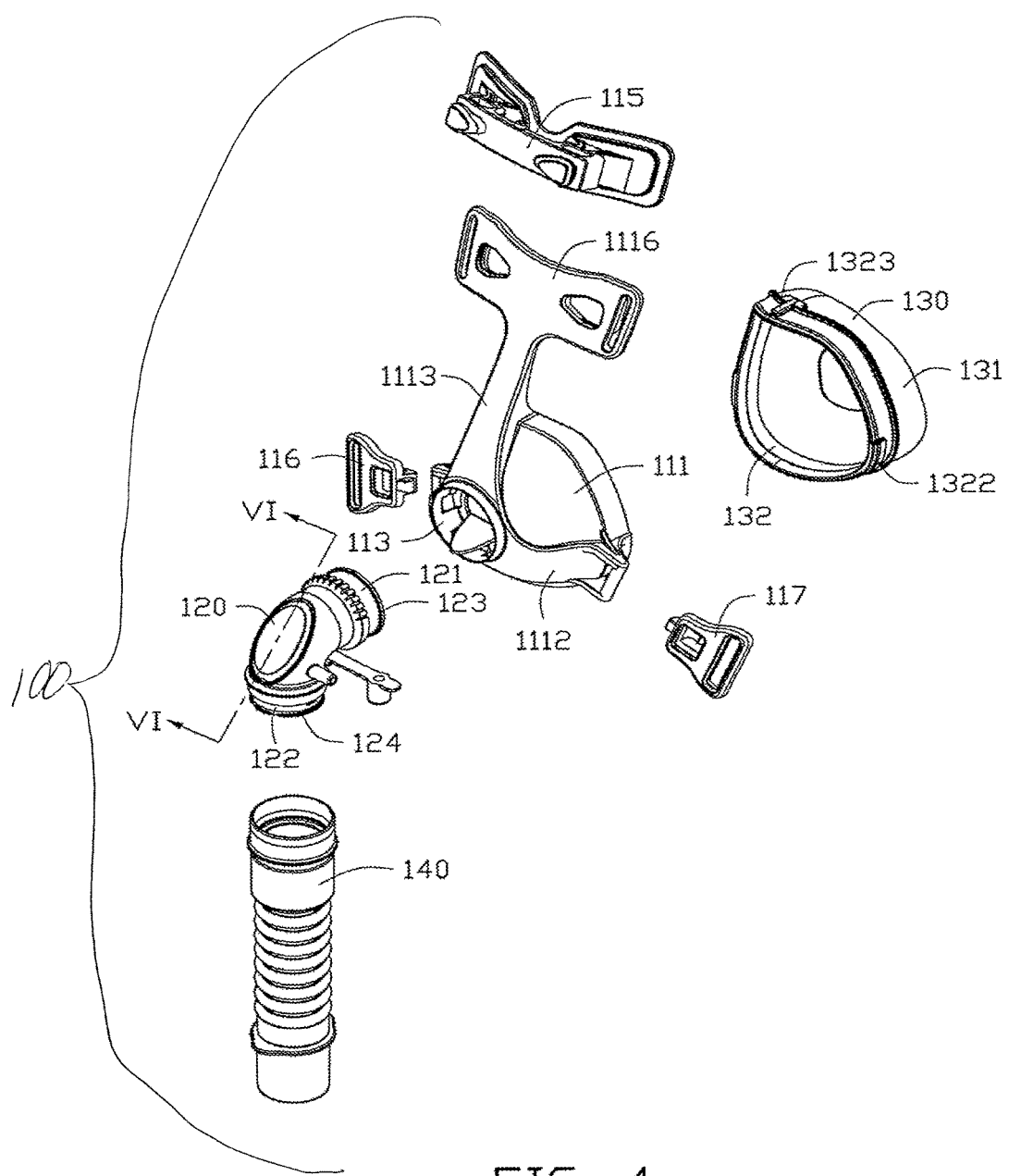
FIG. 4 is another exploded perspective view of the respiratory mask in FIG. 1.

Referring to FIGS. 2-4, the frame 110 has a front surface 111 and a rear surface 112. The front surface 111 defines a connecting hole 113 to connect with the elbow 120. The rear surface 112 defines a receiving chamber 114 for an user to breathe. In this embodiment, the frame 110 described here can be in any shape such as a trapezoidal, triangular or user face contour structure. The cushion 130 has a face-contacting side 131 and a non face-contacting side 132. The non face-contacting side 132 is engaged with the frame 110. In this embodiment, the non face-contacting side 132 has three positioning protrusions 1321 on an outer surface thereof. The three positioning protrusions 1321 are received in the first to third positioning portions 1122, 1123, and 1124 of the frame 110 respectively. The positioning protrusion 1321 can provide positioning function and/or provide securing means to secure the cushion 130 to the frame 110. Therefore, the cushion 130 can be securely engaged with the frame 110.

A respiratory mask assembly includes a frame, a cushion, a forehead member (not annotated) and straps (not shown) for securing the mask to the head. Referring also to FIGS. 2-3, the frame 110 has a connecting portion 1116 to connect with a forehead pad 115. The forehead pad 115 is made of flexible material to avoid discomfort and irritation when using. By reducing unwanted localized contact pressure or forces in the facial contacting regions, especially to the sensitive nasal bridge region of the user, the forehead pad 115 provides the user with comfort while maintaining a serviceable seal. The connecting portion 1116 and the forehead pad 115 can be undetachably or detachably engaged with the frame 110. The connecting portion 1116 further connects with straps (not shown) for securing the frame 110 to the head.

In at least one embodiment, the straps or portions of the straps may be made of or include at least one layer which imparts a degree of stiffness to provide added stability to the respiratory mask assembly, possibly obviating the need for a forehead pad 115. At least a portion of the straps may be formed of a relatively more rigid material in comparison to other portions formed of a relatively more flexible material, providing a multiple layer structure to ensure comfort and stability.

Figure 11:
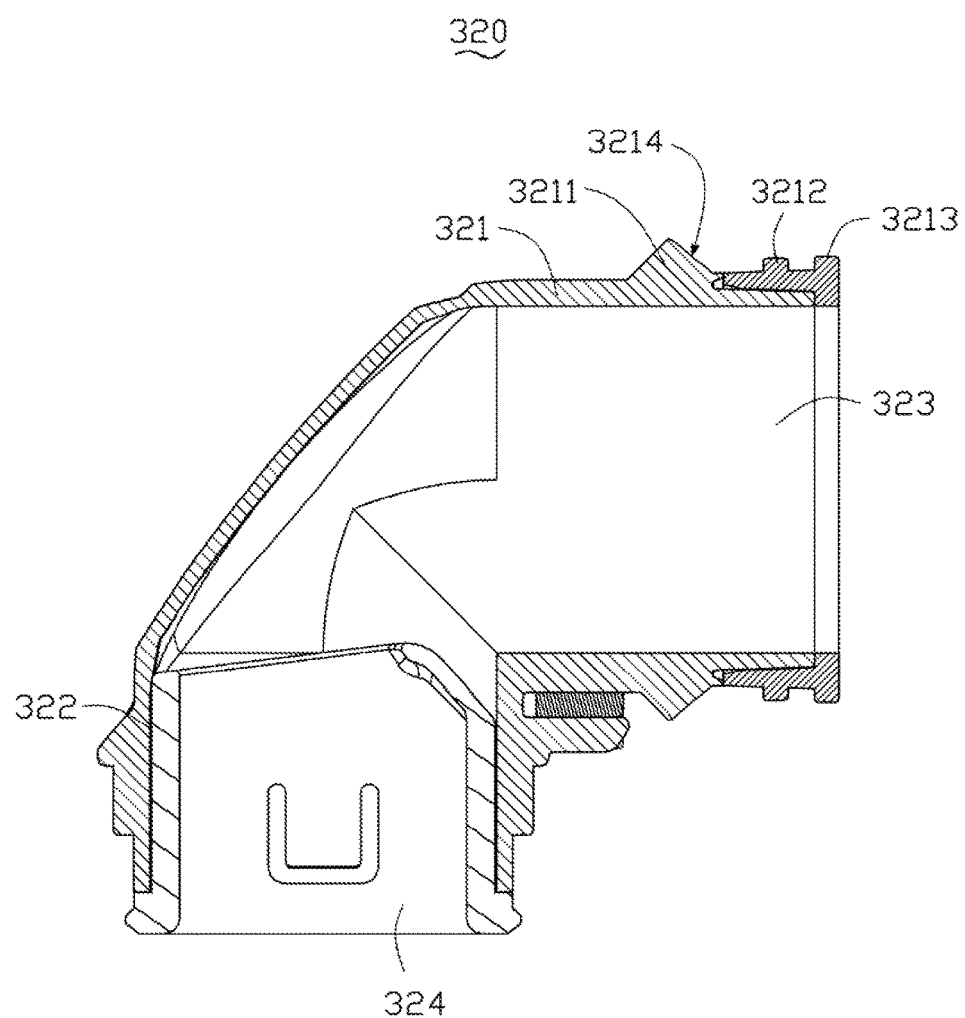
FIG. 11 is a cross sectional view of an elbow in accordance with a third embodiment of the present disclosure.
Figure 12:
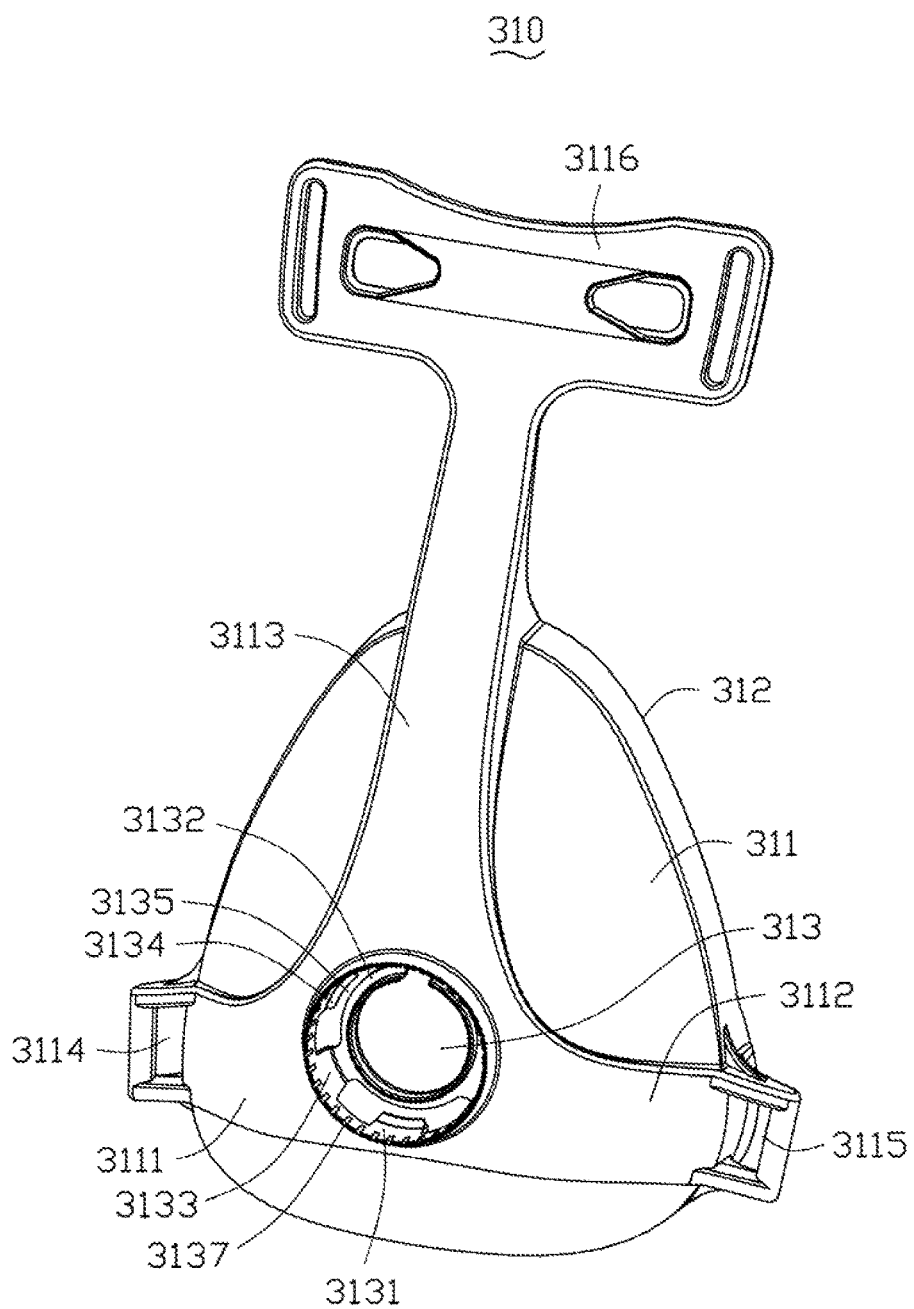
FIG. 12 is an isometric view of a frame in accordance with a third embodiment of the present disclosure.

Referring to FIGS. 11-12, a frame 310 and an elbow 320 in accordance with a third embodiment is provided. The frame 310 and the elbow 320 can replace the frame 110 and the elbow 120 in the first embodiment. The frame 310 has a front surface 311 and a rear surface 312. The front surface 311 defines a connecting hole 313 to connect with the elbow 320. The rear surface 312 is configured to connect with the cushion 130. The frame 310 has three strengthening ribs 3111, 3112, and 3113 on the front surface 311. The first strengthening rib 3111 extends to a left side of the frame 310, and has a first locking member 3114 at one end away from the frame 310. The second strengthening rib 3112 extends to a right side of the frame 310, and has a second locking member 3115 at one end away from the frame 310. The third strengthening rib 3113 extends to an upper side of the frame 310, and is connected to a connecting portion 3116. The first strengthening rib 3111, the second strengthening rib 3112 and the third strengthening rib 3113 have a curvature to follow a user's facial contour. The connecting hole 313 includes a side wall 3131 and an annular ring 3132 located at a bottom of the connecting hole 313. The annular ring 3132 is connected with the side wall 3131 via three connecting portions 3133. Three protrusions 3134 extend inwardly from the side wall 3131, and each of the protrusions 3134 is located between two adjacent connecting portions 3133. An extending length of the protrusions 3134 is shorter than an extending length of the connection portion 3133, which positions the annular ring 3132 closer to a user's face than the protrusions 3134. Therefore, a gap 3135 is formed between the protrusions 3134 and the annular ring 3132. The elbow 320 includes a first end portion 321 and a second end portion 322. The first end portion 321 is configured to connect with the frame 310. The second end portion 322 is configured to connect with the air delivery conduit 140. The first end portion 321 defines an exhaust port 323, and the second end portion 322 defines an intake port 324. Air from the air delivery conduit 140 enters the elbow 320 from the intake port 324 and flows out of the elbow 320 through the exhaust port 323. A plurality of grooves 3137 are formed on the inner edge of the connecting hole 313 such that the air in the receiving chamber communicates with the external air through the grooves 3137. The first end portion 321 includes an engagement mechanism to engage with the connecting hole 313 of the frame 310. Specifically, the engagement mechanism includes a main flange 3211, a first rim 3212 and a second rim 3213. The main flange 3211 is located away from the exhaust port 323, the second rim 3213 is located adjacent to the exhaust port 323, and the first rim 3212 is located between the main flange 3211 and the second rim 3213. The main flange 3211 has a diameter lager than the first rim 3212 and the second rim 3213. When the first end portion 321 of the elbow 320 is inserted into the connecting hole 313, the second rim 3213 is located in the gap 3135 between the annular ring 3132 and the protrusions 3134 inside the connecting hole 313. The protrusions 3134 inside the connecting hole 313 are located between the first rim 3212 and the second rim 3213. The first rim 3212 and the second rim 3213 thus sandwich the protrusions 3134 and provide an enhanced stability to the engagement between the frame 310 and the elbow 320. The first rim 3212 and the second rim 3213 provide means to engage and secure the elbow 320 to the frame 310, that is the first rim 3212 resists the sidewall 3131, and the main flange 3211 is located at outside of the connecting hole 313 and wraps the grooves 3137 but does not seal the grooves 3137 from the outside of the connecting hole 313, which allows fluidic communication between the external air and the air in the receiving chamber and/or allows exhaled air from an user to be washed out to the external air. Therefore, the arrangement can have more than two flanges to securely engage with the frame, or can have only one flange to engage with the frame. The engagement between the elbow and the frame can be either detachable or non-detachable. The path provided by the first end portion 321 and the grooves 3137 formed on the side wall 3131 of the connecting hole 313 cooperatively define a plurality of air flow paths for air washout of exhaled air. In addition, when the elbow 320 is connected with the frame 310, the grooves 3137, and a slope 3214 between the main flange 3211 and the first rim 3212 cooperatively defines a venting pathway to vent air washout of exhale air. In at least one embodiment the grooves are configured to be formed on the frame instead of the elbow, which is opposite arrangement of the previous embodiment.

Figure 5:
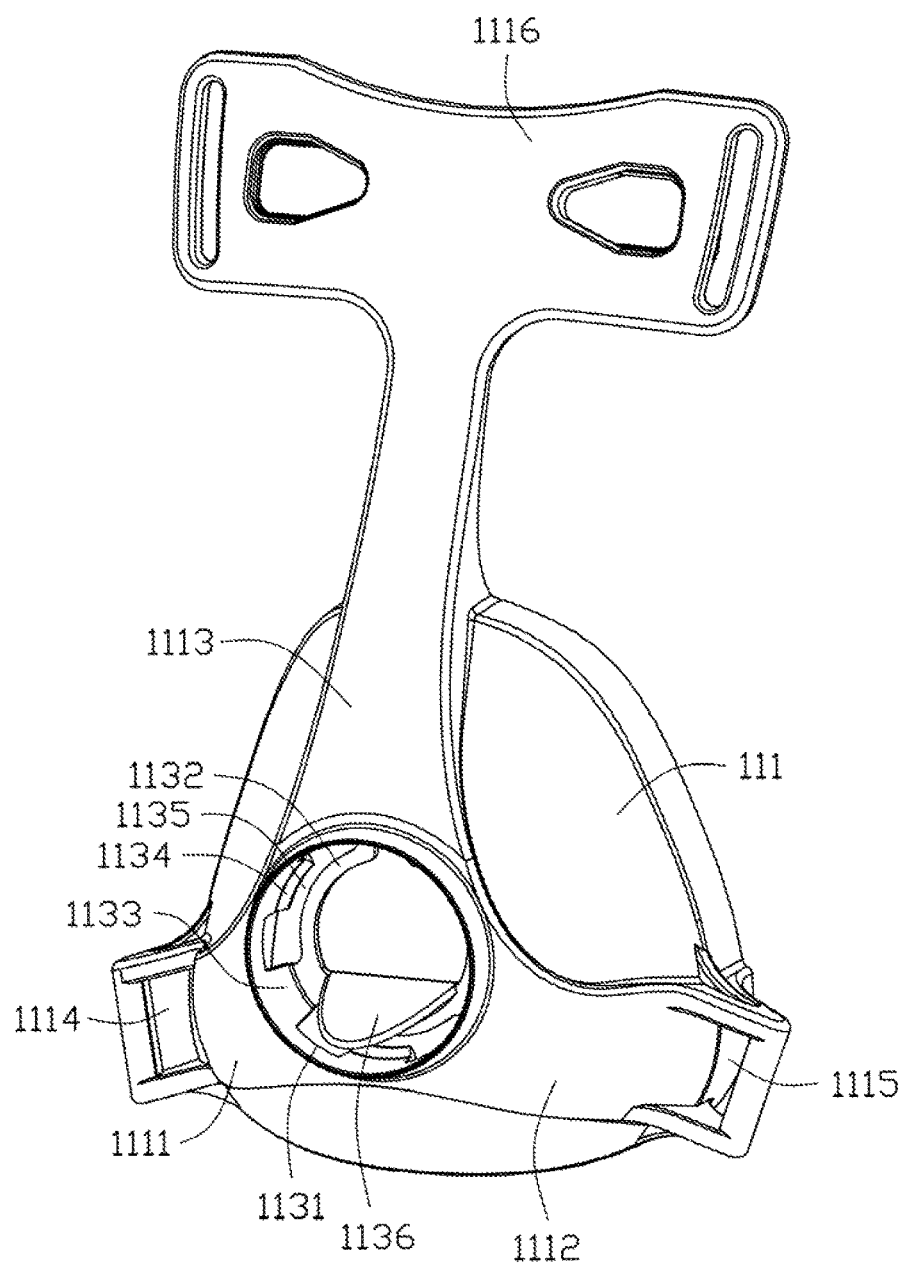
FIG. 5 is an isometric view of a frame in FIG. 3.
Figure 6:
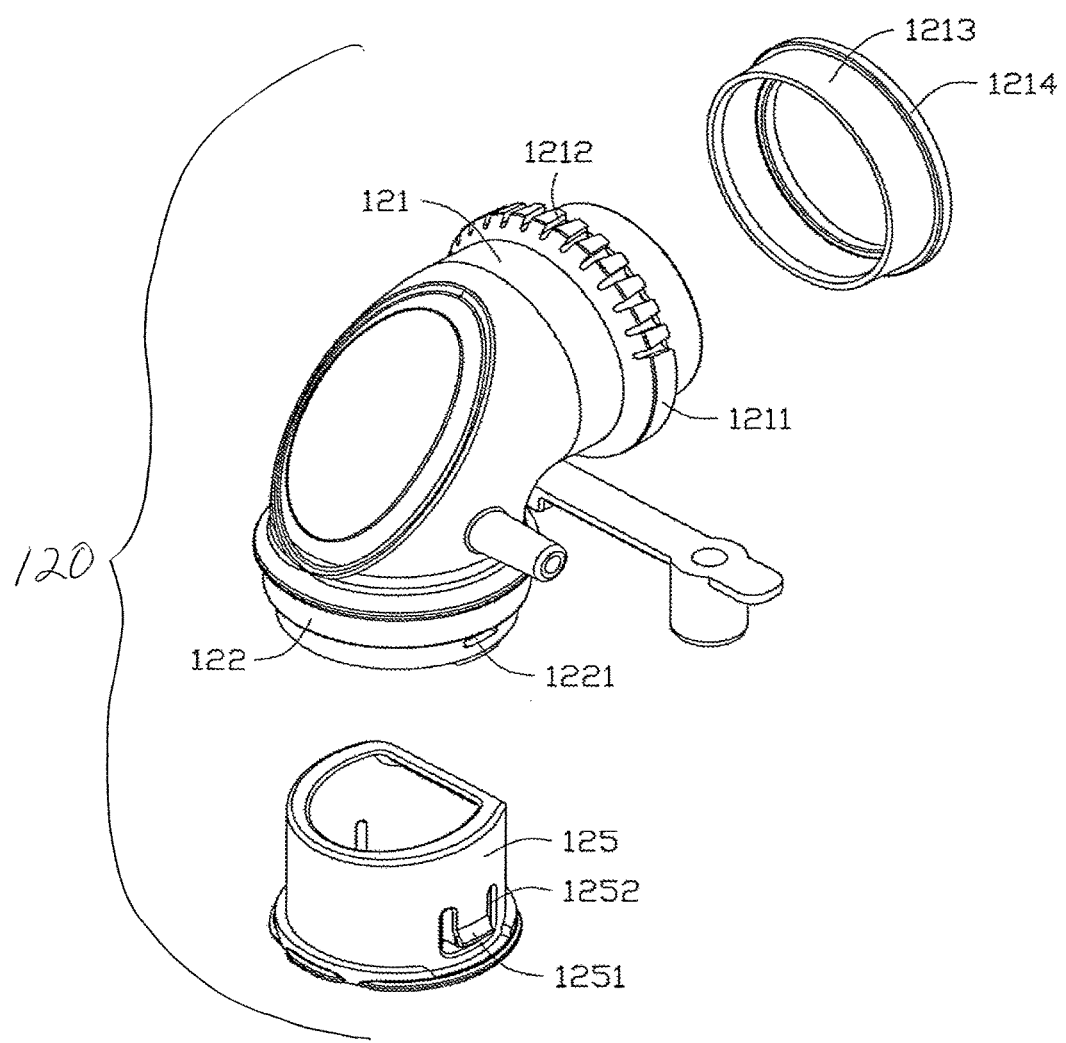
FIG. 6 is an exploded perspective view of the elbow in FIG. 3.
Figure 7:
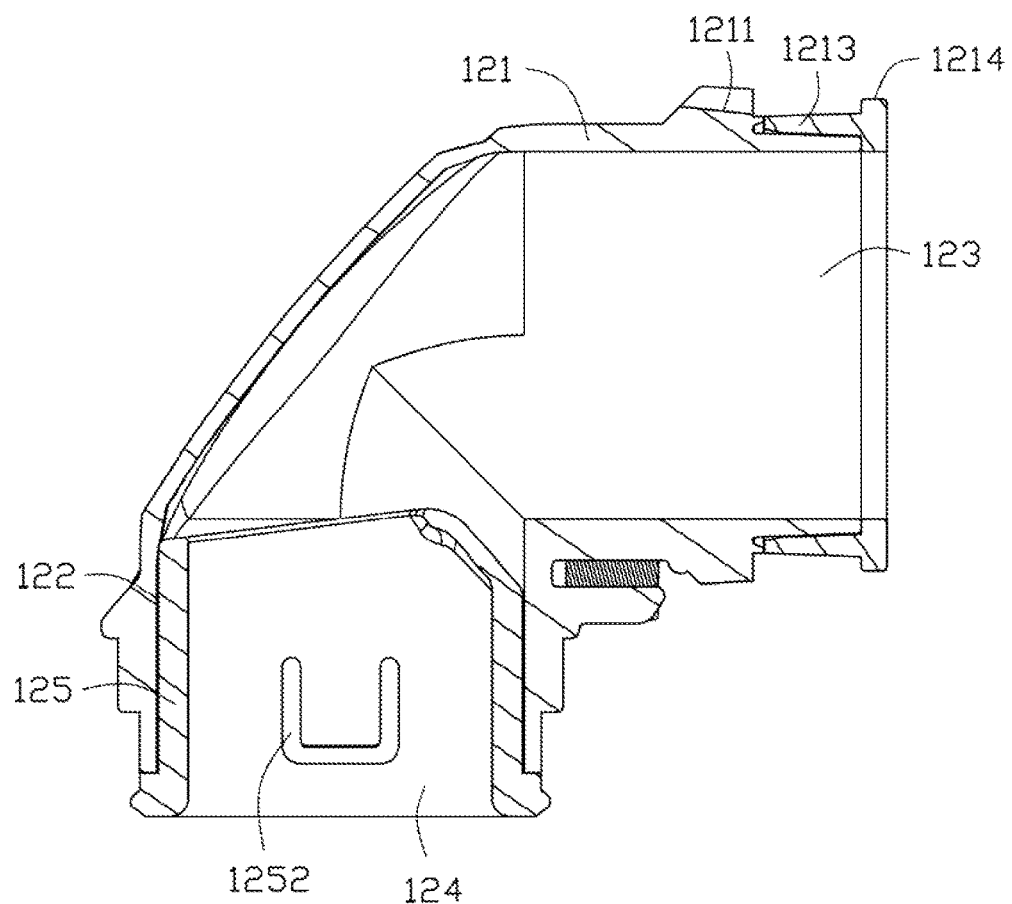
FIG. 7 is a cross sectional view of the elbow in FIG. 3.

Referring to FIGS. 3 and 5, the connecting hole 113 is in communication with the receiving chamber 114 at the rear surface 112. The connecting hole 113 includes a side wall 1131 and an annular ring 1132 located at a bottom of the connecting hole 113 close to the rear surface side. The annular ring 1132 is connected with the side wall 1131 via three connecting portions 1133. Three protrusions 1134 extend inwardly from the side wall 1131, and each of the protrusions 1134 is located between two adjacent connecting portions 1133. In one embodiment, the annular ring is spaced from the rear surface side of the connecting hole and is connected to the side wall via a plurality of connecting portions, a plurality of protrusions extend inwardly from the side wall, the protrusions and the connecting portions form a comb-like structure around the connecting hole. An extending length of the protrusions 1134 into the receiving chamber 114 is shorter than an extending length of the connecting portions 1133, which positions the annular ring 1132 closer to the cushion 130 than the protrusions 1134. Therefore, a gap 1135 is formed between the protrusions 1134 and the annular ring 1132. An air guiding plate 1136 is formed inside the connecting hole 113. The air guiding plate 1136 extends obliquely and downwardly from the annular ring 1132 to the front surface 111 of the frame 110 to deliver and guide air from the elbow 120 to the receiving chamber 114. The air guiding plate 1136 can be formed at any position around the connecting hole 113 and the annular ring 1132. The air guiding plate 1136 and the protrusions 1134 can also be integrally formed or detachably and securely engaged with the annular ring 1132. In at least one embodiment, the air guiding plate extends from the annular ring toward the side wall of the connecting hole.

Referring also to FIGS. 3 and 5, the frame 110 defines a receiving groove 1121 on the user face contacting side of the frame 110 thereof. The receiving groove 1121 is capable of engaging with the cushion 130. In at least one embodiment, the receiving groove 1121 includes three positioning portions 1122, 1123, and 1124. The first positioning portion 1122 and the second positioning portion 1123 are located in a position corresponding to the first strengthening rib 1111 and the second strengthening rib 1112 respectively. The third positioning portion 1124 is located in a position corresponding to the third strengthening rib 1113. The first to third positioning portions 1122, 1123, and 1124 slightly protrude out of the edge of the frame 110, and are configured to engage the frame 110 with the cushion 130 precisely. The positioning portions provides 1122, 1123 and 1124 positioning function and may also provide securing means to the engagement.

Referring to FIGS. 3 and 5-7, the elbow 120 includes a first end portion 121 and a second end portion 122. The first end portion 121 is configured to connect with the frame 110. The second end portion 122 is configured to connect with an air delivery conduit 140 directly or indirectly. The first end portion 121 defines an exhaust port 123, and the second end portion 122 defines an intake port 124. Air from the air delivery conduit 140 enters the elbow 120 from the intake port 124 and flows out of the elbow 120 through the exhaust port 123. The first end portion 121 includes a main flange 1211. The main flange 1211 defines a plurality of grooves 1212 on the outer surface thereof. The grooves 1212 are configured to form flow path. In at least one embodiment, the grooves 1212 have a V-shaped structure. In alternative embodiments, the grooves 1212 can also form as a rectangle structure, a semi-circle structure or a U-shaped structure. As depicted in FIGS. 3, 4, 6, 8 and 9, the grooves 1212 may have different cross-sectional areas along the flow path. In one embodiment, the cross-sectional area close to the front surface 111 is smaller than the cross-sectional area close to the rear surface 112. A connecting ring 1213 can be detachably engaged with or integrally formed on an outer edge of the first end portion 121 of the elbow 120. The connecting ring 1213 has a first flange 1214 to engage in the gap 1135 between the protrusions 1134 and the annular ring 1132 of the connecting hole 113. The connecting ring 1213 described here can be in one piece with the elbow 120 or in separate pieces. In assembling of the frame 110 and the elbow 120, the first end portion 121 of the elbow 120 is inserted into the connecting hole 113 of the frame 110. The grooves 1212 and the frame 110 cooperatively define air flow path for air washout of exhaled air. The first flange 1214 of the connecting ring 1213 is received in the gap 1135 between the protrusions 1134 and the annular ring 1132 to secure the elbow 120 to the frame 110. The engagement between the elbow 120 and the frame 110 can be either detachable or undetachable. The second end portion 122 of the elbow 120 is connected with the air delivery conduit 140 by a connecting member 125. The second end portion 122 of the elbow 120 defines two receiving grooves 1221 on the outer surface thereof. The connecting member 125 has protrusions 1251 at a position corresponding to the receiving grooves 1221. In at least one embodiment, the connecting member 125 defines two U-shaped grooves 1252 and forms two elastic plates 1253. Each protrusion 1251 is formed on one end of the elastic plate 1253. When the connecting member 125 is inserted into the second end portion 122 of the elbow 120, the elastic plates 1253 are first pressed inwardly by an inner surface of the second end portion 122 until the protrusions 1251 are engaged with the receiving grooves 1221 of the second end portion 122.

In the respiratory mask 100 described above, by forming a plurality of grooves 1212 on the main flange 1211 of the first end portion 121 of the elbow 120, when the elbow 120 is assembled with the frame 110, the grooves 1212 and the frame 110 cooperatively define an air flow path for air washout of exhaled air. Since the grooves 1212 are defined on an outer edge of the elbow 120. The pluralities of the grooves 1212 can be formed on the upper half of the first end portion 121 to provide an air flow path that would guide the exhaled air away from the air delivery tube. Therefore, the exhaled air exited from the pluralities of the grooves would not strike directly to the air delivery tube and thus would reduce the potential noise. Furthermore, since the air guiding plate 1136 is formed inside the connecting hole 113, when air is delivered from the elbow 120 to the receiving chamber 114, the air can be directed by the air guiding plate 1136 to the user's nasal bridge smoothly, avoiding user discomfort. The guiding path provided by the air guiding plate 1136 can be in any direction as long as the pressurized air are guided away from the nasal nostrils. The obliquity of the air guiding plate 1136 can be defined any angle. In addition, the air guiding plate 1136 together with the side wall 1131, the annular ring 1132, the connecting portions 1133 and the protrusions 1134 would provide a channel that sandwiches the first end portion 121 and thus provide a stable engagement between the frame 110 and the elbow 120.

Figure 8:
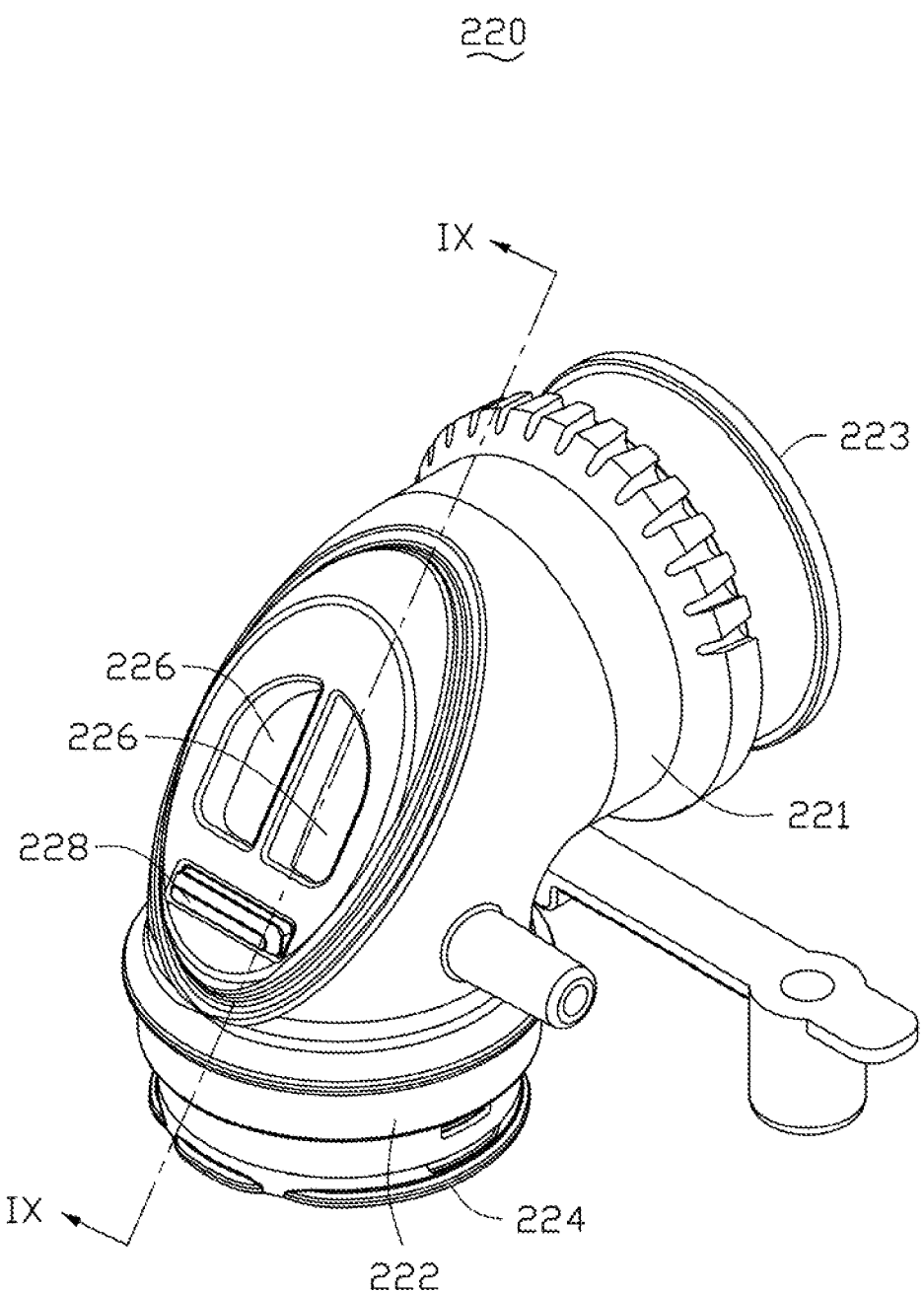
FIG. 8 is an isometric view of a elbow in accordance with a second embodiment of the present disclosure.
Figure 9:
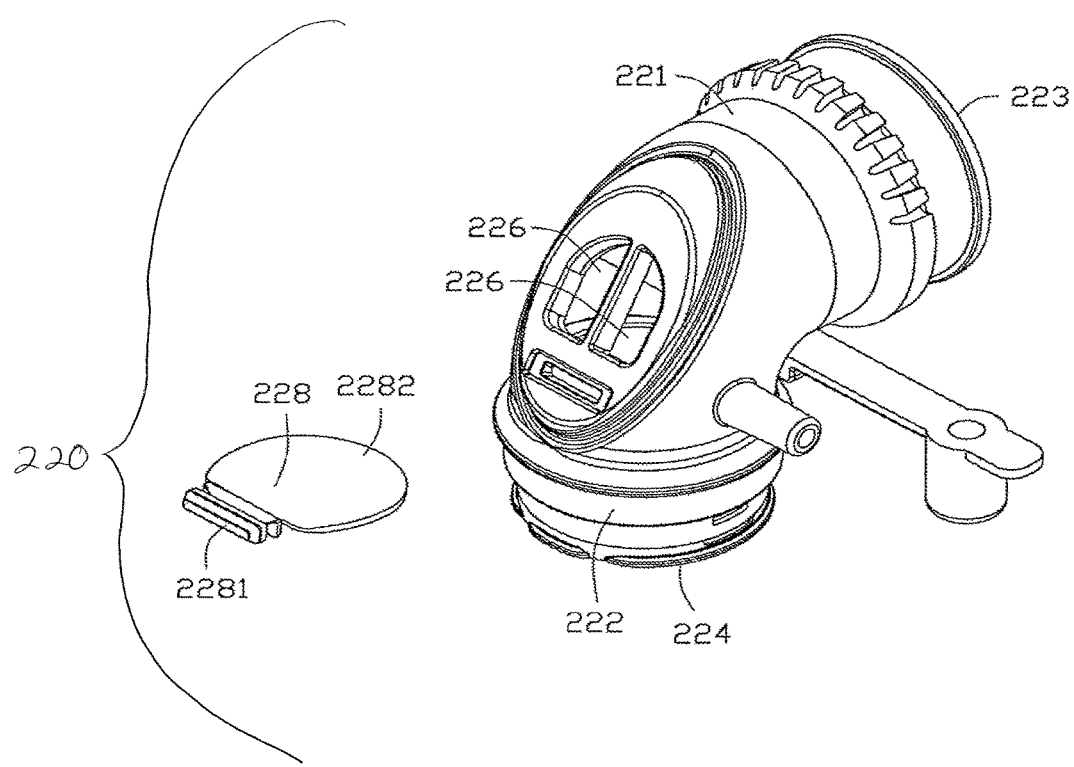
FIG. 9 is an exploded perspective view of the elbow in FIG. 8.
Figure 10:
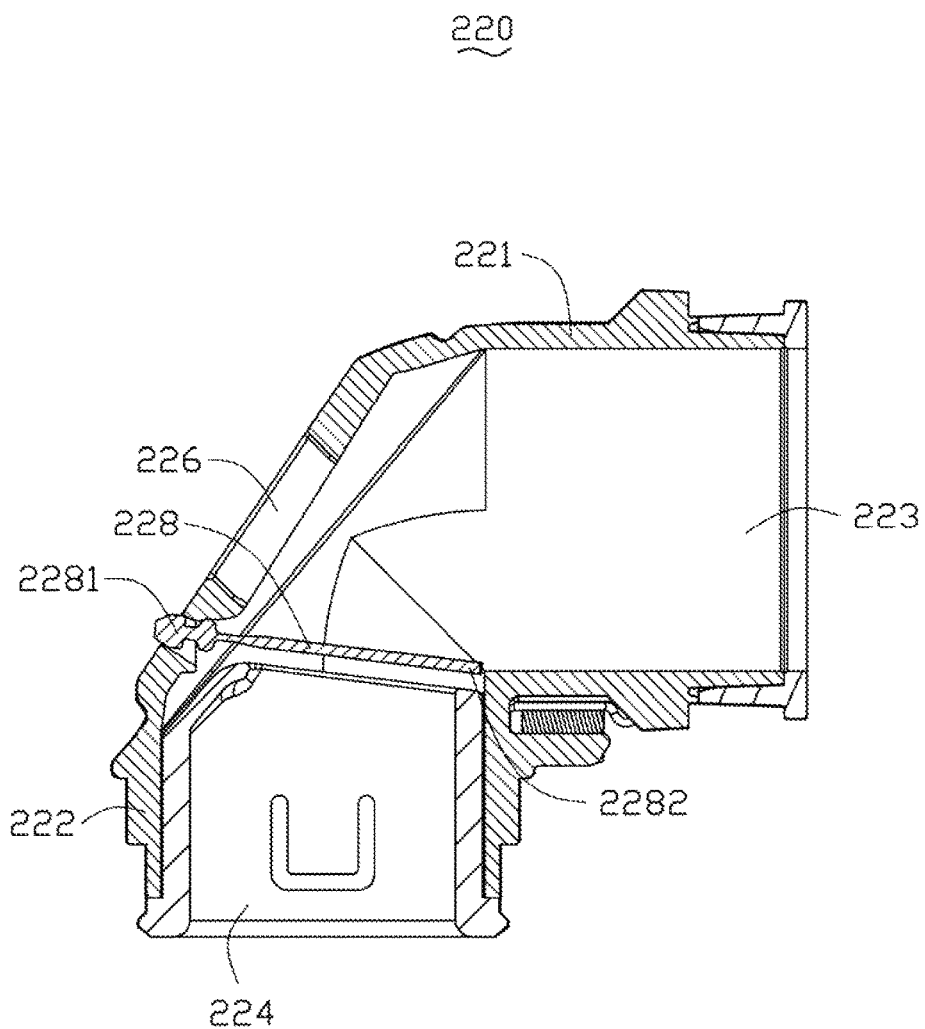
FIG. 10 is a cross sectional view of the elbow in FIG. 8.

Referring to FIGS. 8-10, an elbow 220 in accordance with a second embodiment is provided. The elbow 220 can replace the elbow 120 in the respiratory mask 100. The elbow 220 has a structure similar to the elbow 120 in the first embodiment. The elbow 220 includes a first end portion 221 and a second end portion 222. The first end portion 221 is configured to connect with the frame 110. The second end portion 222 is configured to connect with an air delivery conduit 140. The first end portion 221 defines an exhaust port 223, and the second end portion 222 defines an intake port 224. Air from the air delivery conduit 140 enters the elbow 220 from the intake port 224 and flows out of the elbow 220 through the exhaust port 223. The anti-asphyxia valve 226 is formed on an upper surface of the elbow 220. A hole 227 is defined under the anti-asphyxia valve 226. A flap 228 has a first end 2281 received in the hole 227 and a second end 2282 rotatable around the first end 2281. When air is delivered from the air delivery conduit 140 to the intake port 224, the air pushes the flap 228 to flex upwardly to cover the anti-asphyxia valve 226. Therefore, the flap 228 can prevent air from washing out of the elbow 220 through the anti-asphyxia valve 226 when in use. If no air is provided from the air delivery conduit 140, the flap 228 will flex back to its normal position and leave the anti-asphyxia valve 226 open, which the anti-asphyxia valve 226 thus could communicate the receiving chamber with external air to provide circulating air to a user. Therefore, the anti-asphyxia valve 226 can prevent asphyxia when there is no air provided in the air delivery conduit 140. The anti-asphyxia valve is optional and can be left out if desired.

The frame 110 and straps are connected with connections positioned in an intuitive location for quick and convenient attachment and/or detachment by the user, while maintaining stability to ensure the respiratory mask assembly will not be easily detached accidentally. The straps may include connector members that can be quickly and easily attached and/or detached from the straps and/or the frame 110, providing a release mechanism for the user to conveniently disengage from the respiratory mask assembly. In at least one embodiment, the release mechanisms may include at least one connector portion detachably engaged or formed in one piece with the frame 110, and a mating connector portion detachably engaged or formed in one piece with the straps. The connector members described here can be, but not limited to, locking members 1114 and 1115 and buckles 116 and 117, or buttons, latches, adhesives, magnetic couplers, hook and loop material such as VELCRO®. The forehead pad 115, the buckles 116 and 117, the connector members and/or straps are included or integrated in the respiratory mask assembly to provide the user with comfort, stability, ease of use, and adjustability.

Referring to FIGS. 4-5, the frame 110 has three strengthening ribs 1111, 1112, and 1113 on the front surface 111. The first strengthening rib 1111 extends to a left side of the frame 110, and has a first locking member 1114 at one end away from the frame 110. The second strengthening rib 1112 extends to a right side of the frame 110, and has a second locking member 1115 at one end away from the frame 110. The third strengthening rib 1113 extends to an upper side of the frame 110, and is connected with a forehead member. The first strengthening rib 1111, the second strengthening rib 1112 and the third strengthening rib 1113 have a curvature to follow the user's facial contour. The first locking member 1114 and the second locking member 1115 are connected to the buckle 116 and the buckle 117 respectively, allowing the straps to secure the respiratory mask 100 to the user's face. The strengthening ribs can also be formed on the rear surface 112.

Figure 13:
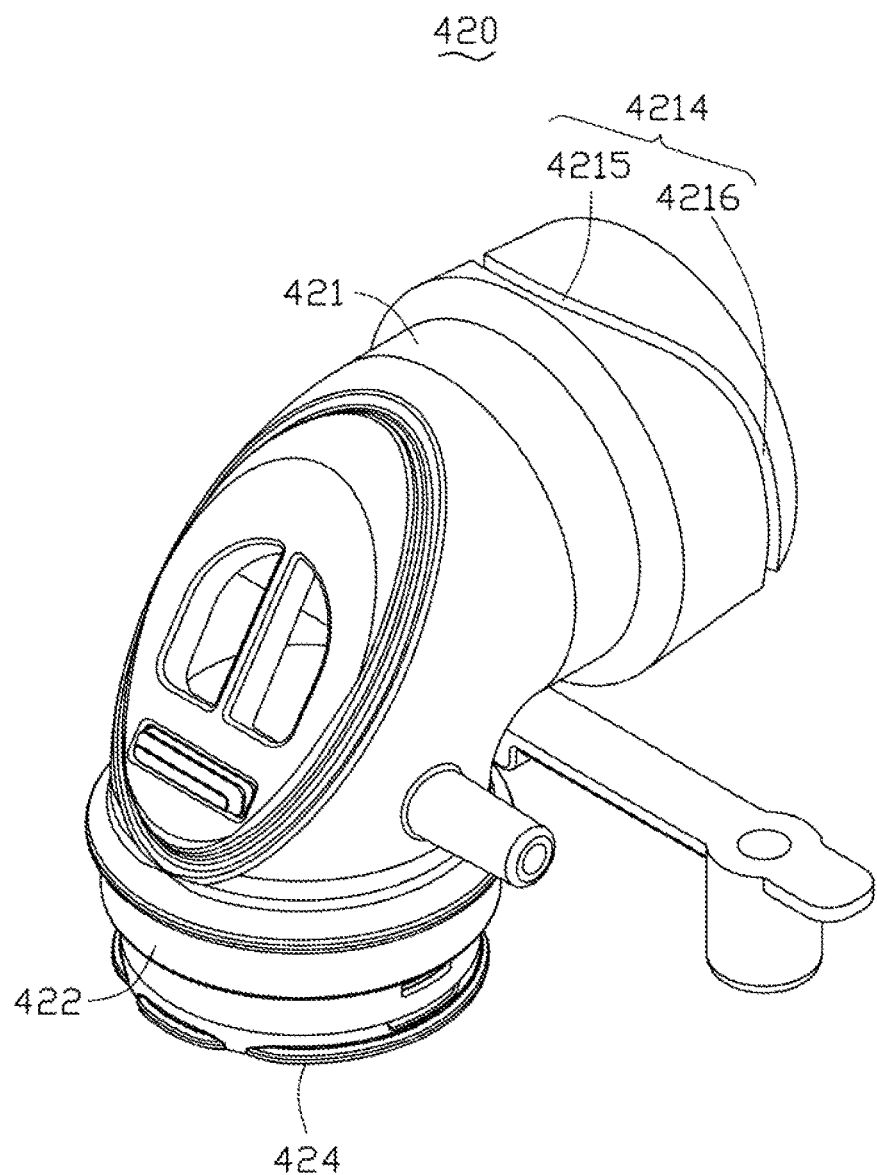
FIG. 13 is an isometric view of an elbow in accordance with a fourth embodiment of the present disclosure.

Referring to FIG. 13, an elbow 420 in accordance with a fourth embodiment is provided. The elbow 420 can replace the elbow 120 in the first embodiment. The elbow 420 includes a first end portion 421 and a second end portion 422. The first end portion 421 is configured to connect with the frame 110. The second end portion 422 is configured to connect with the air delivery conduit 140. The first end portion 421 defines an exhaust port 423, and the second end portion 422 defines an intake port 424. Air from the air delivery conduit 140 enters the elbow 420 from the intake port 424 and flows out of the elbow 420 through the exhaust port 423. An air venting pathway 4214 is formed on an outer surface of the first end portion 421. The air venting pathway 4214 can be of any width and depth, for example 2-6 mm wide and 1-3 mm deep. The width can also be 3 mm and the depth can be 2 mm. The air venting pathway 4214 includes a first section 4215 and a second section 4216. The first section 4215 is in communication with the second section 4216. When the first end portion 421 is inserted into the connecting hole 113 of the frame 110, the first section 4215 is located outside the connecting hole 113 and exposed to the external air, whereas the second section 4216 extends from the first section 4215 to the edge of the first end portion 421. Thus, part of the second section 4216 is located inside of the connecting hole 113 and exposed to the receiving chamber 114. By adopting the structure, exhaled air can be delivered from the second section 4216 to the first section 4215 of the air venting pathway 4214. The air venting pathway 4214 can surround the whole first end portion 421 or can be a single and non-circular path as long as the air venting pathway are capable of communicating the external space to the receiving chamber 114. The first end portion 421 further defines an inserting groove (not shown) at one end adjacent to the exhaust port 423. When the first end portion 421 is inserted into the connecting hole 113 of the frame 110, a C-shaped member (not shown) is compressed to fit within the inserting groove (not shown) to secure the elbow 420 to the frame 110 but still allow the elbow 420 to be freely rotatable around the frame 110. The C-shaped member can be used in combination with the annular ring and the air guiding plate as described in other embodiments. In at least one embodiment, the at least one air venting pathway can also be formed on the side wall, the at least one air venting pathway includes a first portion and a second portion, the second portion is in fluidic communication with the first portion, the first portion is exposed to external air the receiving chamber when the elbow is connected to the frame, the second portion is exposed to air inside the receiving chamber, the air venting pathway on the side wall and the first end portion of the elbow cooperatively defines at least one air flow path.

Figure 14:
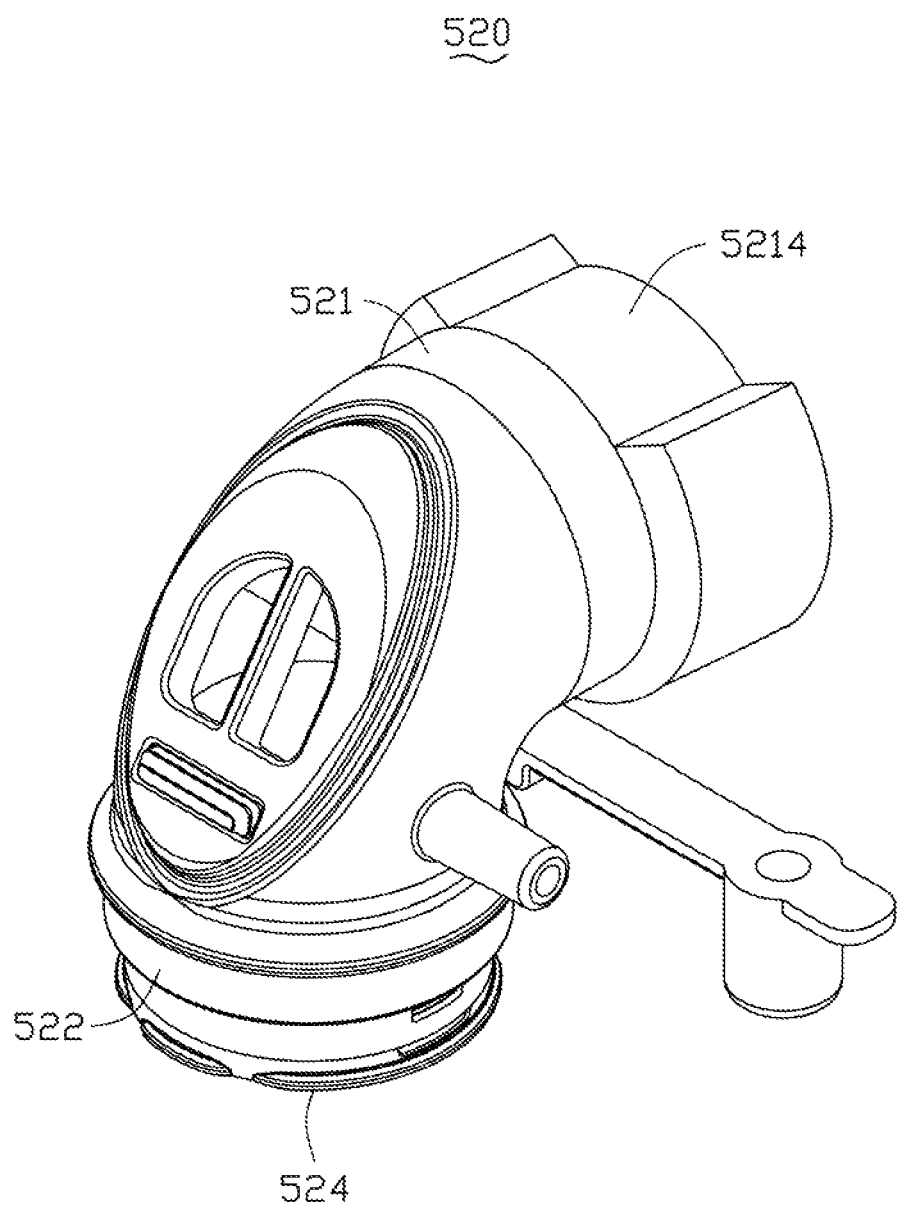
FIG. 14 is an isometric view of an elbow in accordance with a fifth embodiment of the present disclosure.

Referring now to FIG. 14, the fifth embodiment is provided as illustrated. The elbow 520 is similar to the elbow 220 described in the second embodiment. Details are skipped and differences will be described as follow. A first end portion 521 of the elbow 520 is configured to have a single large groove 5214. When the elbow 520 is engaged with the frame, an air flow path would be defined by the groove 5214 and the edge of the connection hole of the frame.

In at least one embodiment, the elbow and the frame have no integrally formed through holes, and air flow path for air washout of exhaled air are only cooperatively formed when the elbow is connected to the frame. The elbow and the frame can be detachably or non-detachably connected, and the elbow can be rotatable, partially rotatable or non-rotatable around the frame. The groove described here can either be located on the edge of the connecting hole or the first end portion of the elbow or formed on both of the edge of the connecting hole or the first end portion.

It is to be further understood that even though numerous characteristics and advantages of the present embodiments have been set forth in the foregoing description, together with details of the structures and functions of the embodiments, the disclosure is illustrative only, and changes may be made in detail, including in matters of shape, size, and arrangement of parts within the principles of the disclosure to the full extent indicated by the broad general meaning of the terms in which the appended claims are expressed.

What is claimed is:

1. A respiratory mask, comprising:
a frame having a front surface and a rear surface, the front surface defining a connecting hole, the rear surface defining a receiving chamber, the connecting hole being in communication with the receiving chamber at the rear surface, wherein the connecting hole comprises a side wall and an annular ring, the annular ring being spaced from the rear surface side of the connecting hole and connected to the side wall via a plurality of connecting portions, a plurality of protrusions extending inwardly from the side wall; and
an elbow having a first end portion, the first end portion being connected with the connecting hole, the first end portion comprising a main flange which defines at least one groove on an outer surface of the main flange;
wherein the elbow and the connecting hole of the frame cooperatively define at least one air flow path communicating air in the receiving chamber with external air.

2. The respiratory mask of claim 1, wherein an extending length of the protrusions into the receiving chamber is shorter than an extending length of the connecting portions, a gap being formed between the protrusions and the annular ring.

3. The respiratory mask of claim 2, wherein a connecting ring is detachably engaged with the first end portion of the elbow or formed integrally with the first end portion of the elbow, the connecting ring comprising a first flange, wherein the first flange is received in the gap when the connecting ring is connected to the respiratory mask.

4. The respiratory mask of claim 2, wherein the first end portion comprises a first rim and a second rim, the protrusions being rotatably retained in a space defined by the first rim and the second rim.

5. The respiratory mask of claim 1, wherein a plate is formed in the connecting hole, the plate extending from the annular ring toward the side wall of the connecting hole.

6. The respiratory mask of claim 1, wherein the first end portion, the at least one groove and the connecting hole cooperatively define the at least one air flow path.

7. The respiratory mask of claim 6, wherein the at least one groove is deployed to reduce noise by avoiding washed out air hitting a part of the respiratory mask, the washed out air being the air washed out of the receiving chamber through the at least one air flow path.

8. The respiratory mask of claim 6, wherein the at least one air flow path is formed on one side of the first end portion of the elbow opposite to an extending direction of a second end portion of the elbow.

9. The respiratory mask of claim 1, wherein at least one groove is defined on the side wall, the connecting hole, the at least one groove and the first end portion cooperatively defining the at least one air flow path.

10. The respiratory mask of claim 9, wherein the first end portion comprises a main flange, a first rim and a second rim, the protrusions being rotatably retained in a space defined by the first rim and the second rim, the second rim being received in the gap between the annular ring and the protrusions inside the connecting hole when the connecting ring is connected to the respiratory mask, the first rim resisting the sidewall where the grooves located, and the main flange being located at outside of the connecting hole and wrapping the grooves without sealing the grooves from the outside of the connecting hole.

11. The respiratory mask of claim 9, wherein the at least one groove is deployed to reduce noise by avoiding washed out air hitting a part of the respiratory mask, the washed out air being the air washed out of the receiving chamber through the at least one air flow path.

12. The respiratory mask of claim 9, wherein the at least one groove has at least two different cross-sectional areas.

13. The respiratory mask of claim 9, wherein the at least one air flow path is formed on one side of the first end portion of the elbow opposite to an extending direction of the second end portion of the elbow.

14. The respiratory mask of claim 1, wherein at least one air venting pathway is formed on an exterior surface of the first end portion, the at least one air venting pathway comprising a first portion and a second portion, the second portion being in fluidic communication with the first portion, the first portion being exposed to external air out of the receiving chamber when the elbow is connected to the frame, the second portion being exposed to air inside the receiving chamber, the first end portion, the air venting pathway and the connecting hole cooperatively defining the at least one air flow path.

15. The respiratory mask of claim 14, wherein the at least one air flow path is so formed that both the elbow and the frame have no constant venting through holes.

16. The respiratory mask of claim 1, wherein at least one air venting pathway is formed on the side wall, the at least one air venting pathway comprising a first portion and a second portion, the second portion being in fluidic communication with the first portion, the first portion being exposed to external air out of the receiving chamber when the elbow is connected to the frame, the second portion being exposed to air inside the receiving chamber, the air venting pathway on the side wall and the first end portion of the elbow cooperatively defining the at least one air flow path.

17. The respiratory mask of claim 16, wherein the at least one air flow path is so formed that both the elbow and the frame have no constant venting through holes.

18. A respiratory mask, comprising:
a frame having a front surface and a rear surface, the front surface defining a connecting hole, the rear surface defining a receiving chamber, the connecting hole being in communication with the receiving chamber at the rear surface, wherein the connecting hole comprises a side wall and an annular ring, the annular ring being spaced from the rear surface side of the connecting hole and connected to the side wall via a plurality of connecting portions, a plurality of protrusions extending inwardly from the side wall; and
an elbow having a first end portion, the first end portion being connected with the connecting hole;
wherein the elbow and the connecting hole of the frame cooperatively define an air intake path and an air exhaled path independent from each other, the air exhaled path being located at a periphery of the air intake path.

19. A respiratory mask, comprising:
a frame having a front surface and a rear surface, the front surface defining a connecting hole, the rear surface defining a receiving chamber, the connecting hole being in communication with the receiving chamber at the rear surface, wherein the connecting hole comprises a side wall and an annular ring, the annular ring being spaced from the rear surface side of the connecting hole and connected to the side wall via a plurality of connecting portions, a plurality of protrusions extending inwardly from the side wall; and
an elbow having a first end portion, the first end portion being connected with the connecting hole;
wherein the first end portion and the frame cooperatively define at least one air flow path communicating air in the receiving chamber with external air;
wherein the at least one air flow path is so formed that both the elbow and the frame have no constant venting path through rotating the elbow in the frame.

20. A respiratory mask, comprising:
a frame having a front surface and a rear surface, the front surface defining a connecting hole, the rear surface defining a receiving chamber, the connecting hole being in communication with the receiving chamber at the rear surface, wherein the connecting hole comprises a side wall and an annular ring, the annular ring being spaced from the rear surface side of the connecting hole and connected to the side wall via a plurality of connecting portions, a plurality of protrusions extending inwardly from the side wall; and
an elbow having a first end portion, the first end portion being connected with the connecting hole, the first end portion comprising a main flange which defines at least one groove on an outer surface of the main flange, wherein the at least one groove has at least two different cross-section areas.

21. The respiratory mask of claim 20, wherein the cross-sectional area of the groove close to the front surface is smaller than the cross-sectional area of the groove close to the rear surface.

* * * * *